United States Patent
Tsuzuki et al.

(12)

(10) Patent No.: US 6,544,953 B2
(45) Date of Patent: Apr. 8, 2003

(54) OPHTHALMIC COMPOSITION

(75) Inventors: Akira Tsuzuki, Nagoya (JP); Sadayasu Tanikawa, Kasugai (JP)

(73) Assignee: Menicon Co., Ltd., Nagoya (JP)

( * ) Notice: Subject to any disclaimer, the term of this patent is extended or adjusted under 35 U.S.C. 154(b) by 0 days.

(21) Appl. No.: 09/833,621

(22) Filed: Apr. 13, 2001

(65) Prior Publication Data

US 2003/0022943 A1 Jan. 30, 2003

(51) Int. Cl.[7] .............................................. A61K 31/70
(52) U.S. Cl. .......................... 514/25; 514/723; 514/912
(58) Field of Search ........................ 514/25, 723, 912

(56) References Cited

FOREIGN PATENT DOCUMENTS

EP    1 050 304    11/2000

OTHER PUBLICATIONS

JP Abstract 403145432A. Fukahori et al., 1991.*

Patent Abstracts of Japan, JP 07 048595, Feb. 21, 1995.

Patent Abstracts of Japan, JP 08 333268, Dec. 17, 1996.

* cited by examiner

Primary Examiner—Zohreh Fay
(74) Attorney, Agent, or Firm—Oblon, Spivak, McClelland, Maier & Neustadt, P.C.

(57) ABSTRACT

An ophthalmic composition which contains a component A consisting of at least one member selected from the group consisting of polyoxyalkylene block copolymers and their derivatives, and a component B consisting of at least one member selected from the group consisting of glycyrrhizic acid and its salts.

30 Claims, 1 Drawing Sheet

OPHTHALMIC COMPOSITION

BACKGROUND OF THE INVENTION

1. Field of the Invention

The present invention relates to an ophthalmic composition, particularly an ophthalmic composition having an excellent cleaning effect and in addition, an adequate safety for the eye, and specifically it relates to an ophthalmic solution such as eye drops and an agent for contact lenses such as a cleaning solution for contact lenses.

2. Discussion of Background

Conventionally, contact lenses have been classified into water-nonabsorptive contact lenses and water-absorptive contact lenses, and classified into hard contact lenses and soft contact lenses. On each of these contact lenses, a stain of e.g. lipids (eye lipids) derived from the tear may be deposited when the lens is put on the eye in some cases, and such a stain on the lens due to the tear may cause deterioration in comfortableness in wearing or eye problems such as failure of eyesight or congestion of cornea, and accordingly it is essential to apply a cleaning treatment to a contact lens in order to safely and comfortably use the contact lens every day.

For such a cleaning treatment of a contact lens, a proper cleaning solution for contact lenses having a cleaning or removing effect over a stain is usually used. As such a cleaning solution for contact lenses, various solutions having a surfactant as a cleaning component added and incorporated therein have been proposed, and one having a polyoxyalkylene block copolymer such as a polyoxyethylene-polyoxypropylene block copolymer or a derivative thereof incorporated may, for example, be known.

However, with respect to the cleaning solution containing a polyoxyalkylene block copolymer or its derivative as a cleaning component, importance is usually attached to safety for the eye, and the concentration of the cleaning component in the solution is suppressed to be as low as possible so that the standards for contact lenses such as diameter or base curve will not change and the shape or physical properties of the contact lenses will not be impaired. At such a low concentration of the cleaning component, no adequate cleaning power such as lipid-solubilizing power may be obtained. Accordingly, there is a fear that when a cleaning treatment of a contact lens is carried out by using such a cleaning solution, a stain of e.g. lipids tends to remain and be deposited on the contact lens, and the eye may harmfully be influenced.

On the other hand, JP-A-7-48595 proposes a solution for contact lenses containing, as an essential component to prevent inflammation of the eye, glycyrrhizic acid or its salt known as a therapeutic agent for e.g. inflammation or allergy from a long time ago, or glycyrrhetinic acid or its derivative, derived from glycyrrhizic acid. It has been clarified that glycyrrhizic acid or its salt has a structure comprising a hydrophobic triterpenoid compound and a hydrophilic glucuronic acid bonded by an ether linkage, and thus it has surface active properties, and accordingly a solution employing glycyrrhizic acid or its salt as a surfactant may have a cleaning effect over a stain.

Accordingly, the present inventors have conducted various studies on said glycyrrhizic acid and its salts and as a result, found that solutions having them alone incorporated therein have a low or no lipid-solubilizing power, and their cleaning effect over a stain of lipids is inadequate.

SUMMARY OF THE INVENTION

Under these circumstances, the present inventors have further conducted extensive studies and as a result, found that the above glycyrrhizic acid and its salts have an effect to significantly improve the lipid-solubilizing power which the above polyoxyalkylene block copolymer or its derivative possesses, and with a solution comprising at least one member selected from the group consisting of glycyrrhizic acid and its salts, together with at least one member selected from the group consisting of polyoxyalkylene block copolymers and their derivatives, both useful cleaning effect over a stain of lipids and reduction in toxicity against the eye can be achieved.

Accordingly, the present invention has been accomplished on the basis of the above discoveries, and it is an object of the present invention to provide an ophthalmic composition which is excellent in a cleaning effect over a stain in the eye or a stain on a contact lens, particularly a stain of lipids, and with which safety for the eye can adequately be secured.

According to the present invention, there is provided an ophthalmic composition which contains a component A consisting of at least one member selected from the group consisting of polyoxyalkylene block copolymers and their derivatives, and a component B consisting of at least one member selected from the group consisting of glycyrrhizic acid and its salts.

DETAILED DESCRIPTION OF THE PREFERRED EMBODIMENTS

Figure 1:
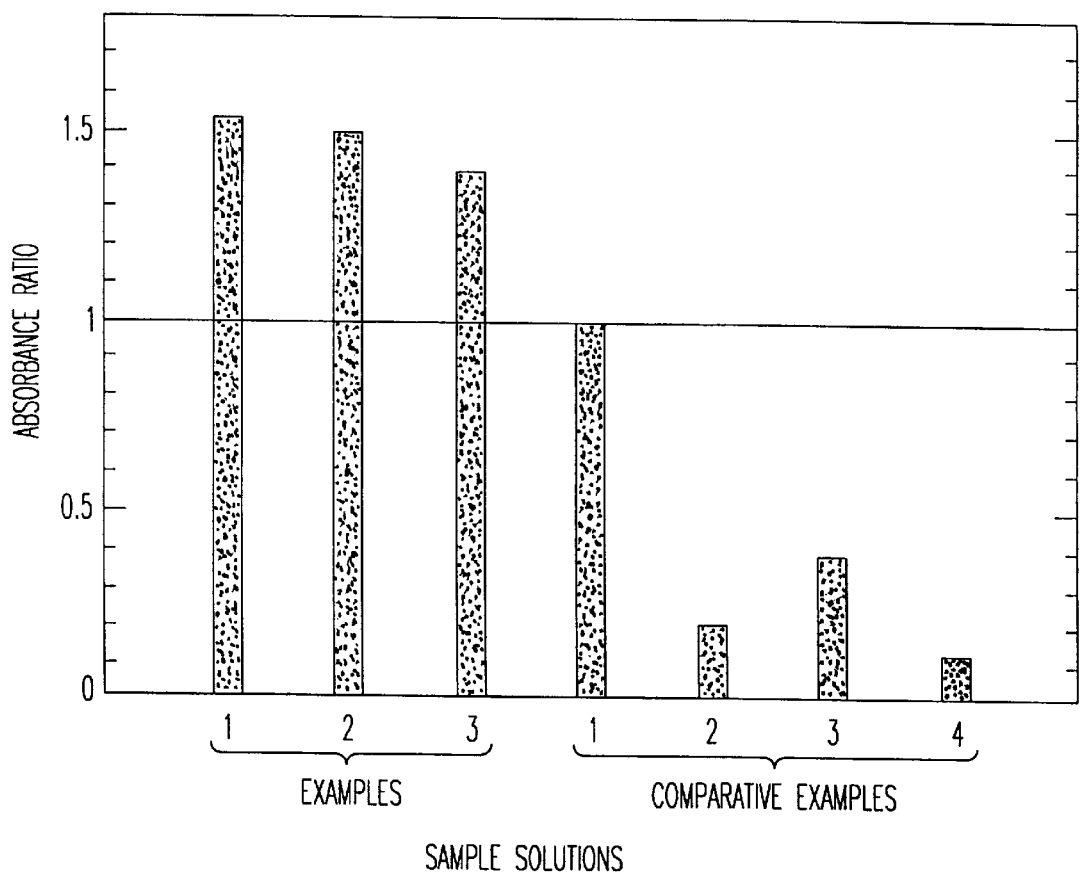
FIG. 1 is a bar graph illustrating absorbance ratios of sample solutions obtained in Examples.

In the ophthalmic composition of the present invention, at least one member selected from the group consisting of polyoxyalkylene block copolymers and their derivatives as the component A and at least one member selected from the group consisting of glycyrrhizic acid and its salts as the component B are incorporated in combination as essential components, whereby the lipid-solubilizing power which the component A originally possesses is effectively reinforced. Accordingly, while securing adequate safety for the eye by properly adjusting the concentration of the component A, an excellent cleaning or removing effect over a stain in the eye or a stain on a contact lens, particularly a stain due to the tear attached to a contact lens, and particularly a stain of lipids, can advantageously be realized.

In a preferred embodiment of the ophthalmic composition according to the present invention, as the above component A, a polyoxyethylene-polyoxypropylene block copolymer or its derivative is advantageously used, and the polyoxyethylene-polyoxypropylene block copolymer or its derivative is preferably one having a HLB value of from 2 to 40.

In another preferred embodiment of the present invention, the above component A is contained preferably in a proportion of from 0.01 to 5.0 w/v %, and the above component B is contained preferably in a proportion of from 0.01 to 1.0 w/v %. By employing such contents, safety for the eye can advantageously be secured, and the cleaning effect over a stain of lipids can more advantageously be obtained.

Further, the ophthalmic composition of the present invention may further contain, in addition to the above components A and B, at least one member selected from the group consisting of a preservative, a thickener, a buffering agent, a chelating agent, an isotonicity agent and a surfactant as the case requires, and by addition of such an additive component, a further function depending upon the component such as a function of preserving a contact lens may advantageously be imparted.

Further, in another preferred embodiment of the present invention, the above ophthalmic composition has an adequate safety for the eye and can thereby be used as an ophthalmic solution. By using this, an effect of glycyrrhizic acid or its salt to prevent inflammation of the eye, as a therapeutic agent for e.g. inflammation or allergy, can be obtained, and in addition, a stain attached on the eye can advantageously be cleaned or removed. Further, the ophthalmic composition of the present invention may be administered to the eye having a contact lens put thereon, whereby the contact lens can be cleaned.

Further, in another preferred embodiment of the present invention, the above ophthalmic composition can preferably be used as an agent for contact lenses. Further, it is also preferred to use said agent for contact lenses as a cleaning solution for contact lenses for cleaning a contact lens taken off from the eye, by bringing the contact lens into contact with said cleaning solution for contact lenses.

The ophthalmic composition of the present invention contains the component A, as one of essential components, consisting of a polyoxyalkylene block copolymer or its derivative or a combination thereof, and thereby shows good surface active effect.

In the present invention, as the polyoxyalkylene block copolymer or its derivative as the component A, ophthalmologically acceptable known high-molecular compounds having a structure or a partial structure comprising two types of polyoxyalkylene groups, one showing hydrophilicity and the other showing lipophilicity, or more polyoxyalkylene groups, aligned and connected in a block, are advantageously employed. Among such high-molecular compounds, more preferred is one wherein each of the above at least two types of polyoxyalkylene groups has a carbon number of from 2 to 4, and particularly preferred is a polyoxyethylene-polyoxypropylene block copolymer or its derivative, which has a polyoxyethylene (POE) chain composed of a polyoxyethylene group and a polyoxypropylene (POP) chain composed of a polyoxypropylene group, or a polyoxyethylene-polyoxypropylene block copolymer addition product of ethylenediamine.

Here, as the polyoxyethylene-polyoxypropylene block copolymer, Pluronic, Pluronic R, Tetronic and Tetronic R (manufactured by BASF, Germany) which are commercially available as nonionic surfactants, and known polymers such as Poloxamer, may, for example, be employed, and among them, use of Poloxamer 124, Poloxamer 188, Poloxamer 237, Poloxamer 338, Poloxamer 407, Tetronic 904, Tetronic 908 or Tetronic 1107 may be recommended.

As a specific example of the derivative of the polyoxyethylene-polyoxypropylene block copolymer used as the component A, a high-molecular compound obtained by etherification or esterification of a hydroxyl group on one or each terminal of a polyoxyethylene-polyoxypropylene block copolymer by a conventional modification means may be mentioned, and its representative examples include POE-POP type ones such as polyoxyethylene-polyoxypropylene monoalkyl ether, polyoxyethylene-polyoxypropylene dialkyl ether, polyoxyethylene-polyoxypropylene monoalkyl ester and polyoxyethylene-polyoxypropylene dialkyl ester, and POE-POP-POE type ones.

Here, among such polyoxyethylene-polyoxypropylene block copolymer derivatives, the POE-POP type one may be represented by any of the following general formulae (a) to (h).

(a) RO—(OE)$_x$—(OP)$_y$—H
(b) HO—(OE)$_x$—(OP)$_y$—R
(c) RCOO—(OE)$_x$—(OP)$_y$—H
(d) HO—(OE)$_x$—(OP)$_y$—COR
(e) RO—(OE)$_x$—(OP)$_y$—R'
(f) RO—(OE)$_x$—(OP)$_y$—COR'
(g) RCOO—(OE)$_x$—(OP)$_y$—R'
(h) RCOO—(OE)$_x$—(OP)$_y$—COR'

In the above general formulae (a) to (h), OE is an oxyethylene group (—CH$_2$CH$_2$O—), OP is an oxypropylene group (—CH$_2$CH(CH$_3$)O—), and each of R and R' is a C$_{1-3}$ linear or branched alkyl group, and in the general formulae (e) to (h), R and R' may be the same or different. Further, x and y which are numbers of repetitions of the above OE and OP, are integers of from 5 to 100 and from 1 to 10, respectively.

Specific examples of the polyoxyethylene-polyoxypropylene block copolymer derivatives represented by the above general formulae (a) to (h) include POE(10)POP(4) monocetyl ether, POE(20)POP(4) monocetyl ether, POE(20)POP(8) monocetyl ether, POE(20)POP(6) decyl tetradecyl ether, POE(30)POP(6) decyl tetradecyl ether, POE(10)POP(4) monocetyl ester, POE(20)POP(4) monocetyl ester, POE(20)POP(8) monocetyl ester, POE(20)POP(6) decyl tetradecyl ester, POE(30)POP(6) decyl tetradecyl ester, POE(10)POP(4) monolauryl ether, POE(10)POP(4) monolauryl ester, POE(3)POP(1) cetyl acetate, POE(3)POP(1) isocetyl acetate, POE(3)POP(1) cetyl acetate and POE(3)POP(1) isocetyl acetate.

Further, examples of the POE-POP-POE type high-molecular compounds as representative examples of the polyoxyethylene-polyoxypropylene block copolymer derivatives, include compounds represented by the following general formulae (i) to (n).

(i) RO—(OE)$_a$—(OP)$_b$—(OE)$_a$—H
(j) RO—(OE)$_a$—(OP)$_b$—(OE)$_a$—R'
(k) RCOO—(OE)$_a$—(OP)$_b$—(OE)$_a$—H
(l) RCOO—(OE)$_a$—(OP)$_b$—(OE)$_a$—COR'
(m) OH—(OE)$_a$—(OP)$_b$—(OE)$_a$—R
(n) OH—(OE)$_a$—(OP)$_b$—(OE)$_a$—COR

In the above general formulae (i) to (n), each of OE, OP, R and R' is as defined for the above general formulae (a) to (h), and a and b which are numbers of repetitions of OE and OP, are integers of from 5 to 150 and from 10 to 100, respectively, and preferably a/b=0.5 to 3.5.

Further, other examples of the polyoxyethylene-polyoxypropylene block copolymer derivatives include poloxamine type high-molecular compounds which are tetrafunctional block copolymers obtained by sequentially adding ethylene oxide and propylene oxide to ethylene diamine, represented by the following general formulae (o) to (y).

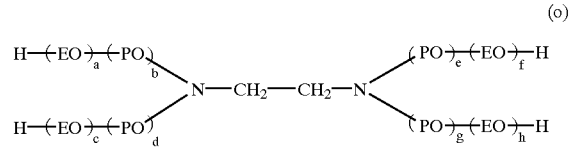

(o)

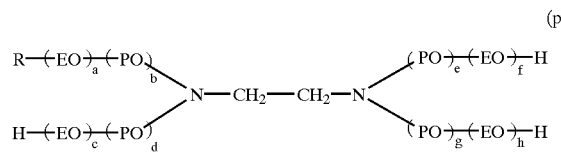 (p)

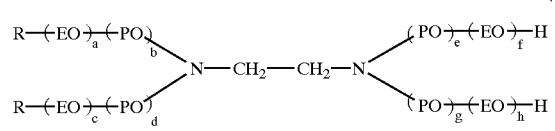 (q)

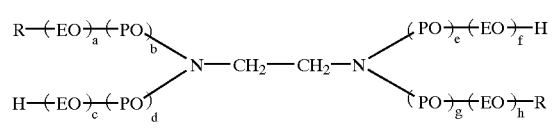 (r)

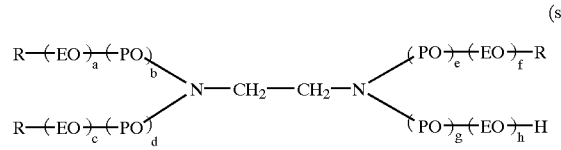 (s)

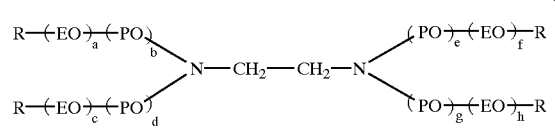 (t)

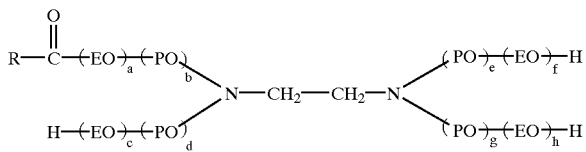 (u)

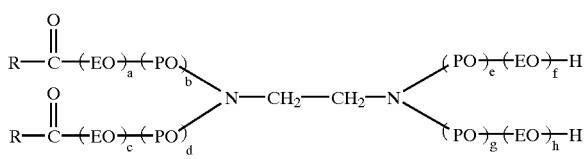 (v)

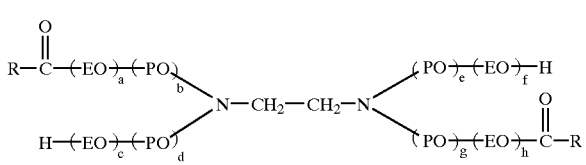 (w)

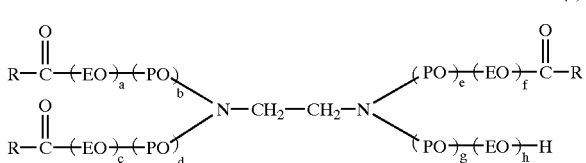 (x)

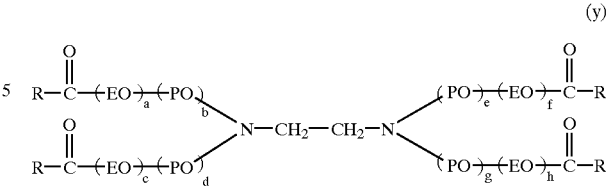 (y)

In the above general formulae (o) to (y), R is as defined above, each of a, c, f and h is an integer of from 1 to 150, and each of b, d, e and g is an integer of from 2 to 50, and preferably a/b=0.015 to 30.

In the present invention, the polyoxyethylene-polyoxypropylene block copolymer or its derivative preferably has a value of HLB (hydrophile-lipophile balance) of from 2 to 40, suitably from 7 to 30, in view of the purpose of the present invention of realizing an excellent cleaning effect.

In the ophthalmic composition of the present invention containing at least one member of such specific high-molecular compounds as the component A, at least one member selected from the group consisting of glycyrrhizic acid and its salts as the component B coexists, whereby cleaning power, particularly lipid-solubilizing power, based on the surface active property of the component A is significantly reinforced, and accordingly a cleaning effect can be obtained even when the content of the component A is suppressed to a low concentration, specifically to a concentration of a level of 0.01 w/v %. Accordingly, in the present invention, the component A is used at a concentration of usually at least 0.01 w/v %, preferably at least 0.1 w/v %, more preferably at least 0.3 w/v %. However, if the content is too high, the eye may be irritated, the cytotoxicity tends to be high, and the safety for the body tends to decrease, and accordingly as the upper limit, the concentration is usually at most 5.0 w/v %, preferably at most 3.0 w/v %, more preferably at most 2.0 w/v %.

The glycyrrhizic acid or its salt as the component B to be incorporated in the ophthalmic composition of the present invention together with the component A synergically improves cleaning power such as lipid-solubilizing power which the component A originally possesses, by the combination with the component A, whereby an excellent cleaning effect which can never be expected with the component A alone can be realized.

Examples of the glycyrrhizic acid or its salt include glycyrrhizic acid, glycyrrhizic acid monopotassium, glycyrrhizic acid dipotassium, glycyrrhizic acid monoammonium and glycyrrhizic acid disodium, and one or a combination of at least two among these compounds is used as the component B, and glycyrrhizic acid dipotassium or glycyrrhizic acid disodium is advantageously used.

In the present invention, the amount of the component B may optionally be set taking e.g. the type of the high-molecular compound as the component A into consideration in order that the synergistic cleaning effect as the purpose of addition of the component B can advantageously be realized, and the component B is used at a concentration of usually from 0.01 to 1.0 w/v %, preferably from 0.05 to 0.5 w/v %. However, if the amount of the component B is too small, no adequate effect of improving the cleaning power will be obtained, and on the contrary, if the amount is too large, the safety for the eye may be impaired, or the shape or physical properties of a contact lens may be impaired such that standards for a contact lens such as a diameter or a base curve may be changed.

The ophthalmic composition of the present invention is prepared by adding and incorporating such specific two types of components A and B in proper amounts into a proper aqueous medium in an optional order in a conventional method. In the present invention, in addition to the components A and B, one or more additive components conventionally used for ophthalmic solutions and solutions for contact lenses may further be incorporated in a conventional amount as the case requires. Such an additive component is preferably one which has a high safety for the body, which is adequately acceptable ophthalmologically, and which has no influence over the shape or physical properties of a contact lens, and used preferably in an amount satisfying such essentialities, whereby a function depending upon the additive component can advantageously be imparted to the cleaning solution without impairing the effects of the present invention.

In order to advantageously impart disinfection effect on the eye or a contact lens, and preservative and preservation effects on the ophthalmic composition, a preservative having a preservative effect may be added to the ophthalmic composition of the present invention. As such a preservative, a proper one may be selected from known preservatives, and used alone or in combination as a mixture of at least two.

As the preservative, sorbic acid, potassium sorbate, benzoic acid or its salt, ethyl parahydroxybenzoate, butyl parahydroxybenzoate, propyl parahydroxybenzoate, methyl parahydroxybenzoate or chlorobutanol may, for example, be mentioned.

Further, in the present invention, a thickener may be added so as to properly adjust the viscosity of the ophthalmic composition, and examples of the thickener include gums such as heteropolysaccharides; synthetic organic high-molecular compounds such as polyvinyl alcohol, poly-N-vinyl pyrrolidone, polyethylene glycol, polypropylene glycol and polyacrylamide; cellulose derivatives such as hydroxyethyl cellulose, hydroxypropyl methylcellulose, carboxymethyl cellulose and methyl cellulose; and starch derivatives.

Further, with respect to the ophthalmic composition of the present invention, if the pH value or the osmotic pressure is too high or too small, there is a fear that the eye may be irritated or eye problems may be caused, and accordingly the pH value of the ophthalmic solution is preferably adjusted within a range of from about 5.3 about 8.5 by addition of a pH adjustor, and the osmotic pressure is preferably adjusted within a range of from about 200 to about 400 mOsm/kg by addition of an isotonicity agent. As the pH adjustor to be used for adjustment of pH, e.g. sodium hydroxide or hydrochloric acid may be used, and as the isotonicity agent to be used for adjustment of the osmotic pressure, at least one compound selected from the group consisting of sodium chloride, potassium chloride, saccharides, sugar alcohols, and polyhydric alcohols and their ethers and esters, is usually used.

In order to keep the pH of the ophthalmic composition within the above effective and ophthalmologically safe range, usually at least one buffering agent may be added. As the buffering agent, a conventionally known one may optionally be selected and used. Specifically, acids such as phosphoric acid, boric acid, carboxylic acid and oxycarboxylic acid, salts thereof (such as sodium salt), and further, Good-Buffer, tris(hydroxymethyl)aminomethane (Tris), bis(2-hydroxyethyl)iminotris(hydroxymethyl)methane (Bis-Tris) and sodium hydrogen carbonate, may, for example, be mentioned from the viewpoint that they have safety for the eye and influences over a contact lens can be minimized.

Further, there is a possibility that e.g. calcium as a stain from the tear may be deposited or adsorbed on a contact lens, particularly on a soft contact lens in general, and accordingly a chelating agent may advantageously be added to the ophthalmic composition to prevent such inconvenience. As the chelating agent, ethylenediaminetetraacetic acid (EDTA) or its salts, such as disodium ethylenediaminetetraacetate (EDTA·2Na) or trisodium ethylenediaminetetraacetate (EDTA·3Na), may, for example, be used.

Further, in the ophthalmic composition according to the present invention, a known surfactant, advantageously a surfactant other than the above component A, may be added and incorporated so long as it does not inhibit the synergistic effect caused by the combination of the components A and B, in an amount not impairing the effect, whereby the cleaning effect over lipids will be more excellent. As the surfactant, preferred is a polyethylene glycol derivative such as a polyoxyethylene alkylphenyl ether formaldehyde condensate represented by tyloxapol, a sorbitan fatty acid ester such as sorbitan monooleate represented by polysorbate 80 or sorbitan sesquioleate, a polyoxyethylene sorbitan fatty acid ester such as sorbitan polyoxyethylene monooleate, a glycerol fatty acid ester such as glyceryl monostearate, a polyethylene glycol fatty acid ester such as polyethylene glycol monostearate, a polyoxyethylene alkyl ether such as polyoxyethylene lauryl ether, or polyoxyethylene castor oil, in view of safety for the body.

As evident from the above explanation, as the aqueous medium to which the above components A and B and another component are added to prepare the ophthalmic composition of the present invention, in addition to water itself such as running water, purified water or distilled water, physiological saline or a sodium chloride-containing aqueous solution, or a known cleaning solution for contact lenses or an ophthalmic solution such as eye drops, may, for example, be employed so long as it is a solution consisting essentially of water.

When a contact lens is cleaned by using the ophthalmic composition of the present invention thus obtained, an optional means may be employed, such as a means of using said ophthalmic composition as a cleaning solution for contact lenses, and soaking a contact lens taken off from the eye in the cleaning solution for contact lenses of the present invention filled in a proper container for a predetermined time, or cleaning the contact lens with said solution by rubbing, or a means of using said ophthalmic composition as an ophthalmic solution and administering it in a proper amount to the eye having a contact lens put thereon so that the contact lens is brought into contact with the ophthalmic composition on the eye and is cleaned. Here, in a case where the ophthalmic composition of the present invention is used as an ophthalmic solution, the eye, in addition to the contact lens, is cleaned of course.

Accordingly, when the eye or contact lens is cleaned by the ophthalmic composition of the present invention, a stain due to the tear such as lipids attached to the eye or contact lens can effectively be removed. Further, as the ophthalmic composition of the present invention has a high safety for the eye, no eye problems or the like will be caused even when the cleaning treatment of a contact lens by soaking or rubbing is carried out for a long period of time, and further when the ophthalmic composition is administered to the eye so as to clean the contact lens on the eye.

Further, needless to say, the contact lens cleaned on the eye or in a state where it is taken off from the eye, can be subjected to a sterilization treatment by e.g. a sterilization solution for contact lenses prepared separately as the case requires.

Further, a contact lens to which the ophthalmic composition of the present invention is applied is not particularly limited, and the ophthalmic composition applies to all types of soft contact lenses including a low water-absorptive type and a high water-absorptive type, and hard contact lenses, and e.g. the material of a contact lens is not limited.

Now, the present invention will be explained in further detail with reference to Examples and Comparative Examples. However, it should be understood that the present invention is by no means restricted to such specific Examples. Further, various changes, modifications or improvements may be made to the present invention other than the following Examples or the above specific description by those skilled in the art without departing from the scope of the present invention.

Test on Cleaning Effect Over Lipids

The cleaning effect of the ophthalmic composition of the present invention over lipids was examined by means of a lipid-solubilizing rate method. Specifically, predetermined additive components were added to purified water in various proportions as identified in the following Tables 1 and 2 to prepare various sample solutions having a pH of 7.3 (Examples 1 to 3 and Comparative Examples 1 to 4) firstly. For the preparation of sample solutions, as essential additive components, Poloxamer 407 (Px407) which is a polyoxyethylene-polyoxypropylene block copolymer as a polyoxyalkylene block copolymer, and glycyrrhizic acid dipotassium (GK2), glycyrrhizic acid disodium (GNa2) or glycyrrhizic acid (GA) were used. Further, as other additive components, hydroxypropyl methylcellulose (HPMC) as a thickener, dihydrate of disodium ethylenediaminetetraacetate (EDTA·2Na·2H$_2$O) as a chelating agent, bis(2-hydroxyethyl)iminotris(hydroxymethyl)methane (Bis-Tris) as a buffering agent and sodium chloride (NaCl) were used. Further, for adjustment of pH, sodium hydroxide or hydrochloric acid was used.

TABLE 1

| Additive | Examples | | |
|---|---|---|---|
| components | 1 | 2 | 3 |
| Px407 | 0.5 | 0.5 | 0.5 |
| GK2 | 0.1 | — | — |
| GNa2 | — | 0.1 | — |
| GA | — | — | 0.1 |
| HPMC | 0.28 | 0.28 | 0.28 |
| EDTA · 2Na · 2H$_2$O | 0.05 | 0.05 | 0.05 |
| Bis-Tris | 0.1 | 0.1 | 0.1 |
| NaCl | 0.87 | 0.87 | 0.87 |

Addition proportion (unit): w/v %

TABLE 2

| Additive | Comparative Examples | | | |
|---|---|---|---|---|
| components | 1 | 2 | 3 | 4 |
| Px407 | 0.5 | — | — | — |
| GK2 | — | 0.5 | — | — |
| GNa2 | — | — | 0.5 | — |
| GA | — | — | — | 0.5 |
| HPMC | 0.28 | 0.28 | 0.28 | 0.28 |
| EDTA · 2Na · 2H$_2$O | 0.05 | 0.05 | 0.05 | 0.05 |
| Bis-Tris | 0.1 | 0.1 | 0.1 | 0.1 |
| NaCl | 0.87 | 0.87 | 0.87 | 0.87 |

Addition proportion (unit): w/v %

Then, using a colored lipid obtained by mixing triglyceride as a lipid and Sudan I as a pigment in a weight ratio of 99:1, 0.5 g thereof was accommodated in a predetermined test bottle, 20 mL of the above obtained sample solution was further added and accommodated in the test bottle, and the opening of the test bottle was covered with a proper lid. This operation was carried out with respect to each of the above sample solutions.

Further, each test bottle having the colored lipid and the sample solution accommodated therein thus prepared, was shaken at a temperature of 25° C. for 24 hours at a constant rate and further left to stand for a predetermined time, and a supernatant fluid in each test bottle was collected, and the absorbance at 485.5 nm was measured with respect to each supernatant fluid by means of a spectrophotometer (recording spectrophotometer UV-2200, manufactured by Shimadzu Corporation).

From the values of the absorbance thus measured, the ratio (relative value) of the absorbance of each sample solution to the absorbance of the sample solution of Comparative Example 1 was obtained, and the results are shown in the following Table 3 and in FIG. 1 as a bar graph. A value of the absorbance ratio higher than the absorbance ratio in Comparative Example 1 i.e. a relatively high absorbance indicates an excellent cleaning effect over lipids, specifically excellent lipid-solubilizing power.

TABLE 3

| | Examples | | | Comparative Examples | | | |
|---|---|---|---|---|---|---|---|
| | 1 | 2 | 3 | 1 | 2 | 3 | 4 |
| Absorbance ratio | 1.54 | 1.50 | 1.40 | 1 | 0.20 | 0.38 | 0.12 |

As evident form the results shown in Table 3 and FIG. 1, it was confirmed that each of the sample solutions of Examples 1 to 3 showed high lipid-solubilizing power as compared with the sample solution of Comparative Example 1 wherein Poloxamer 407 as a polyoxyalkylene block copolymer alone was used and no glycyrrhizic acid or its salt was used together. On the other hand, it was confirmed that each of the sample solutions of Comparative Examples 2 to 4 containing glycyrrhizic acid or its salt but containing no Poloxamer 407, showed significantly low lipid-solubilizing power as compared with the sample solutions of the Examples and even the sample solution of Comparative Example 1, and accordingly, it was found that no adequate desired cleaning effect could be obtained. From these findings, it is estimated that the lipid-solubilizing power of Poloxamer 407 itself can synergistically be increased by incorporating at least one member selected from the group consisting of glycyrrhizic acid and its salts together with Poloxamer 407 in a solvent.

Test on Adjustability to Lenses

To examine the adjustability of the ophthalmic composition of the present invention to contact lenses, the following test was carried out. Namely, in the same manner as in the above test on cleaning effect over lipids, predetermined additive components were added in purified water in proportions as identified in the following Table 4, to prepare various sample solutions having a pH of 7.3 (Examples 4 and 5 and Comparative Example 5).

On the other hand, a plurality of commercially available soft contact lenses (Menicon Soft 72, manufactured by Menicon Co., Ltd., lens diameter: 13.5 mm) were prepared, and such lenses were soaked in physiological saline kept at a temperature of 25° C., and the lens diameters of the contact lenses in a soaked state were measured by means of a projector (universal projector manufactured by Nikon Corporation), and the obtained measured values were recorded as initial values of the lens diameters.

Then, the contact lenses of which the initial values of the lens diameters were thus obtained were soaked in the sample solution prepared as mentioned above at a temperature of 25° C. for 3 days, and the lens diameters were measured in a soaked state by means of the same projector as mentioned above. This operation was carried out by using three contact lenses with respect to each sample solution.

Then, the difference (d) between the measured value of the lens diameter thus obtained (value after the soaking) and the initial value of the lens diameter was obtained in accordance with the following formula:

$$d=(\text{value after the soaking})-(\text{initial value})$$

with respect to each contact lens, and the average value of the obtained values was obtained with respect to each sample solution. The results are shown in the following Table 4 as the change in lens diameter. Needless to say, the smaller the value of the change in lens diameter, the more excellent the adjustability to contact lenses, and further, the value of the change in lens diameter is particularly preferably within ±0.2 mm.

TABLE 4

| Additive components | Examples | | Comparative Example |
| --- | --- | --- | --- |
| | 4 | 5 | 5 |
| Px407 | 0.5 | 0.5 | 0.5 |
| GK2 | 0.1 | 0.3 | — |
| HPMC | 0.28 | 0.28 | 0.28 |
| EDTA · 2Na · 2H$_2$O | 0.05 | 0.05 | 0.05 |
| Bis-Tris | 0.1 | 0.1 | 0.1 |
| NaCl | 0.87 | 0.87 | 0.87 |
| Change in lens diameter (mm) | 0.02 | 0.08 | 0.02 |

Addition proportion (unit): w/v %

As evident form the results shown in the above Table 4, it was confirmed that each of the sample solutions of Examples 4 and 5 had no influence over the shape (diameter) of contact lenses at an equal level to the sample solution of Comparative Example 5 i.e. a conventional sample solution wherein Poloxamer 407 as a polyoxyalkylene block copolymer alone is used and no glycyrrhizic acid or its salt is used together. Accordingly, it is understood that the solutions of the present invention are advantageous in view of the adjustability to contact lenses.

As evident from the above explanation, the ophthalmic composition of the present invention contains as the component A at least one member selected from the group consisting of polyoxyalkylene block copolymers and their derivatives, and contains as the component B at least one member selected from the group consisting of glycyrrhizic acid and its salts together with the component A, whereby the cleaning power of the specific component A is effectively increased, and accordingly both excellent cleaning effect over a stain of e.g. lipids on the eye or a contact lens and a high safety for the eye can be realized.

What is claimed is:

1. An ophthalmic composition, consisting essentially of:
   a) at least one component A selected from the group consisting of polyoxyalkylene block copolymers as a surfactant in an amount of from 0.1 to 5 wt %; and
   b) at least one component B selected from the group consisting of glycyrrhizic acid and ophthalmically acceptable salts thereof.

2. The ophthalmic composition of claim 1, wherein the component A is a polyoxyethylene-polyoxypropylene block copolymer.

3. The ophthalmic composition of claim 2, wherein the polyoxyethylene-polyoxypropylene block copolymer has a HLB value of from 2 to 40.

4. The ophthalmic composition of claim 1, wherein the component B is contained in an amount of from 0.01 to 1.0 w/v %.

5. An ophthalmic composition consisting essentially of:
   a) at least one component A selected from the group consisting of polyoxyalkylene block copolymers as a surfactant in an amount of from 0.1 to 5 wt %;
   b) at least one component B selected from the group consisting of glycyrrhizic acid and ophthalmically acceptable salts thereof and
   c) a preservative, a thickener, a buffering agent, a chelating agent, an isotonicity agent or additional surfactant.

6. The ophthalmic composition of claim 1, wherein the component A is a polyoxyethylene-polyoxypropylene-polyoxyethylene block copolymer.

7. The ophthalmic composition of claim 2, wherein the polyoxyethylene-polyoxypropylene block copolymer comprises polyoxyethylene-polyoxypropylene monoalkyl ether, polyoxyethylene-polyoxypropylene dialkyl ether, polyoxyethylene-polyoxypropylene monoalkyl ester or polyoxyethylene-polyoxypropylene dialkyl ester.

8. The ophthalmic composition of claim 2, wherein the polyoxyethylene-polyoxypropylene block copolymer comprises tetrafunctional block copolymers produced by sequentially adding ethylene oxide and propylene oxide ethylene diamine.

9. The ophthalmic composition of claim 3, wherein said HLB value is from 7 to 30.

10. The ophthalmic composition of claim 1, wherein said component A is present in an amount of from 0.3 to 5 wt. %.

11. The ophthalmic composition of claim 10, wherein said component A is present in an amount of from 0.3 to 3 wt. %.

12. The ophthalmic composition of claim 11, wherein said component A is present in an amount of from 0.3 to 2 wt. %.

13. The ophthalmic composition of claim 4, wherein said component B is present in an amount of from 0.05 to 0.5 w/v %.

14. The ophthalmic composition of claim 1, having a pH of from about 5.3 to about 8.5.

15. An ophthalmic solution, which comprises the ophthalmic composition of claim 1, in a solution consisting essentially of water.

16. The ophthalmic solution of claim 15, wherein said water is selected from the group consisting of purified water, distilled water, physiological saline solution and a sodium chloride-containing aqueous solution.

17. An ophthalmic composition which comprises:
   a) a component A which is at least one polyoxyethylene-polyoxypropylene block copolymer surfactant selected from the group consisting of Poloxamer 124,237,338, 407, and Tetronic 904,908 and 1107; and b) a component B consisting of at least one member selected from the group consisting of glycyrrhizic acid and ophthalmically acceptable salts thereof.

18. The ophthalmic composition of claim 17, wherein the component B is present in an amount of from 0.01 to 1.0 w/v %.

19. The ophthalmic composition of claim 7, which further comprises a preservative, a thickener, a buffering agent, a chelating agent, an isotonicity agent or additional surfactant.

20. The ophthalmic composition of claim 17, wherein said component A is present in an amount of from 0.1 to 5 wt. %.

21. The ophthalmic composition of claim 17, wherein said component B is present in an amount of from 0.05 to 0.5 w/v %.

22. An ophthalmic solution, which comprises the ophthalmic composition of claim 17, in a solution consisting essentially of water.

23. The ophthalmic solution of claim 22, wherein said water is selected from the group consisting of purified water, distilled water, physiological saline solution and a sodium chloride-containing aqueous solution.

24. An ophthalmic solution for cleaning contact lenses, consisting essentially of:

a) at least one component A selected from the group consisting of polyoxyalkylene block copolymer;

b) at least one component A selected from the group consisting of glycyrrhizic acid and salts thereof in c) an ophthalmically-acceptable solution consisting essentially of water.

25. A method of cleaning a contact lens, which comprises contacting said contact lens with an effective amount of the ophthalmic solution, comprising:

a) at least one component A selected from the group consisting of polyoxyalkylene block copolymers as a surfactant in an amount of from 0.1 to 5 wt %; and b) at least one component B selected from the group consisting of glycyrrhizic acid and ophthalmically acceptable salts thereof, in a solution consisting essentially of water.

26. The method of claim 25, wherein said contact lens is in a human eye.

27. The method of claim 25, wherein said contact lens is outside of a human eye.

28. A method of cleaning a contact lens, which comprises contacting said contact lens with an effective amount of the ophthalmic solution of claim 22.

29. The method of claim 28, wherein said contact lens is in a human eye.

30. The method of claim 28, wherein said contact lens is outside of a human eye.

* * * * *